United States Patent [19]
Ota et al.

[11] Patent Number: 5,488,443
[45] Date of Patent: Jan. 30, 1996

[54] PORTABLE LASER APPARATUS FOR OPHTHALMOLOGICAL OPERATION

[75] Inventors: Yasuo Ota, Gamagori; Masanori Enomoto, Nishio; Hitoshi Abe, Okazaki, all of Japan

[73] Assignee: Nidek Co., Ltd., Gamagori, Japan

[21] Appl. No.: 141,539

[22] Filed: Oct. 27, 1993

[30] Foreign Application Priority Data

Nov. 7, 1992 [JP] Japan .................................... 4-322386

[51] Int. Cl.$^6$ .................................................. A61B 3/10
[52] U.S. Cl. ........................ 351/221; 351/205; 351/245; 359/368
[58] Field of Search .................................. 351/221, 205, 351/245, 214; 359/391, 392, 396, 368, 385, 389, 390

[56] References Cited

U.S. PATENT DOCUMENTS

| | | | |
|---|---|---|---|
| 4,477,159 | 10/1984 | Mizuno et al. | 351/214 |
| 4,582,405 | 4/1986 | Miller et al. | |
| 4,824,229 | 4/1989 | Narita et al. | 359/368 |
| 5,337,095 | 8/1994 | Katsuragi et al. | 351/208 |

*Primary Examiner*—William L. Sikes
*Assistant Examiner*—Hung Xuan Dang
*Attorney, Agent, or Firm*—Nikaido, Marmelstein, Murray & Oram

[57] ABSTRACT

A laser apparatus for ophthalmological operation which can be readily handled and moved extremely easily. This apparatus comprises: a laser light source; a microscope unit with an observation optical system for observing an eye to be operated; a laser light guiding optical system for guiding treatment light emitted from the laser light source toward the affected part of the eye to be operated within an observation visual field of the microscope unit; a power source housing for containing a source for supplying electrical power to the microscope unit and the laser light source; conductor cables for connecting the microscope unit and the laser light source to the power source; a base with a friction plate which can be attached to the top surface of the power source housing; and a slide device which includes a joy stick and slides the microscope unit with respect to the base by operating the joy stick.

5 Claims, 9 Drawing Sheets

PORTABLE LASER APPARATUS FOR OPHTHALMOLOGICAL OPERATION

BACKGROUND OF THE INVENTION

1. Industrial Field of the Invention

The present invention relates to a laser apparatus for ophthalmological operation and, more particularly, to an operation apparatus of the type which guides a laser beam to a slit lamp microscope.

2. Description of Related Art

A conventional laser apparatus for ophthalmological operation which guides a laser beam to a slit lamp microscope, has a structure in which a sliding mechanism includes a base which is securely fixed on a mount table, to thereby allow the slit lamp microscope to move back and forth and to the left and right on the base. When a small-sized laser light source such as a semiconductor laser or a mini YAG laser can be acquired, the laser light source is directly incorporated in a housing of the slit lamp microscope. Further, a power source is fixed under the mount table. One example of such apparatus has an outer appearance shown in FIG. 8.

In the case of the above-described apparatus, wheels are provided on the mount table, and consequently, there is no particular trouble in moving the apparatus in a small area. However, it is inconvenient to move the apparatus between places at a considerably long distance. Especially when the apparatus must be carried by stairs, much labor is required, and also, it is rather dangerous for persons to carry the apparatus.

SUMMARY OF THE INVENTION

Taking the problems of the conventional apparatus described above into consideration, the present invention has an object to provide a laser apparatus for ophthalmological operation which can be readily handled and moved extremely easily.

In order to achieve this object, a laser apparatus for ophthalmological operation according to this invention comprises: a laser light source; a microscope unit with an observation optical system for observing an eye to be operated; a laser light guiding optical system for guiding treatment light emitted from the laser light source toward the affected part of the eye to be operated within an observation visual field of the microscope unit; a power source housing for containing a source for supplying electrical power to the microscope unit and the laser light source; conductor cables for connecting the microscope unit and the laser light source to the power source; a base with a friction plate which can be attached to the top surface of the power source housing; and a slide device which includes a joy stick and slides the microscope unit with respect to the base by operating the joy stick.

Also, this laser apparatus for ophthalmological operation may include a container exclusively used for carrying the laser apparatus.

Further, in the laser apparatus for ophthalmological operation according to the invention, the base and a top plate of the power source housing may include means for detachably attaching the base on the top plate.

Moreover, in the laser apparatus for ophthalmological operation, the top plate of the power source housing may also be used as the base.

Furthermore, a laser apparatus for ophthalmological operation according to this invention comprises: a slit lamp microscope unit with an observation optical system for observing an eye to be operated; a laser light source for emitting treatment light which is provided in the slit lamp microscope unit; a laser light guiding optical system for guiding the treatment light emitted from the laser light source toward the affected part of the eye to be operated within an observation visual field of the slit lamp microscope unit; a power source housing for enclosing a source for supplying electrical power to the slit lamp microscope unit and the laser light source; conductor cables for connecting the microscope unit and the laser light source to the power source; a base with a friction plate which can be attached to the top surface of the power source housing; and a slide device which includes a joy stick and slides the microscope unit with respect to the base by operating the joy stick.

This laser apparatus for ophthalmological operation may include a semiconductor light source for emitting an aiming beam which is provided in the slit lamp microscope unit, so that the treatment light and the aiming beam will be made coaxial with each other by a dichroic mirror.

DETAILED DESCRIPTION OF THE PREFERRED EMBODIMENTS

The preferred embodiments of the present invention will be hereinafter described with reference to the attached drawings.

Figure 1:
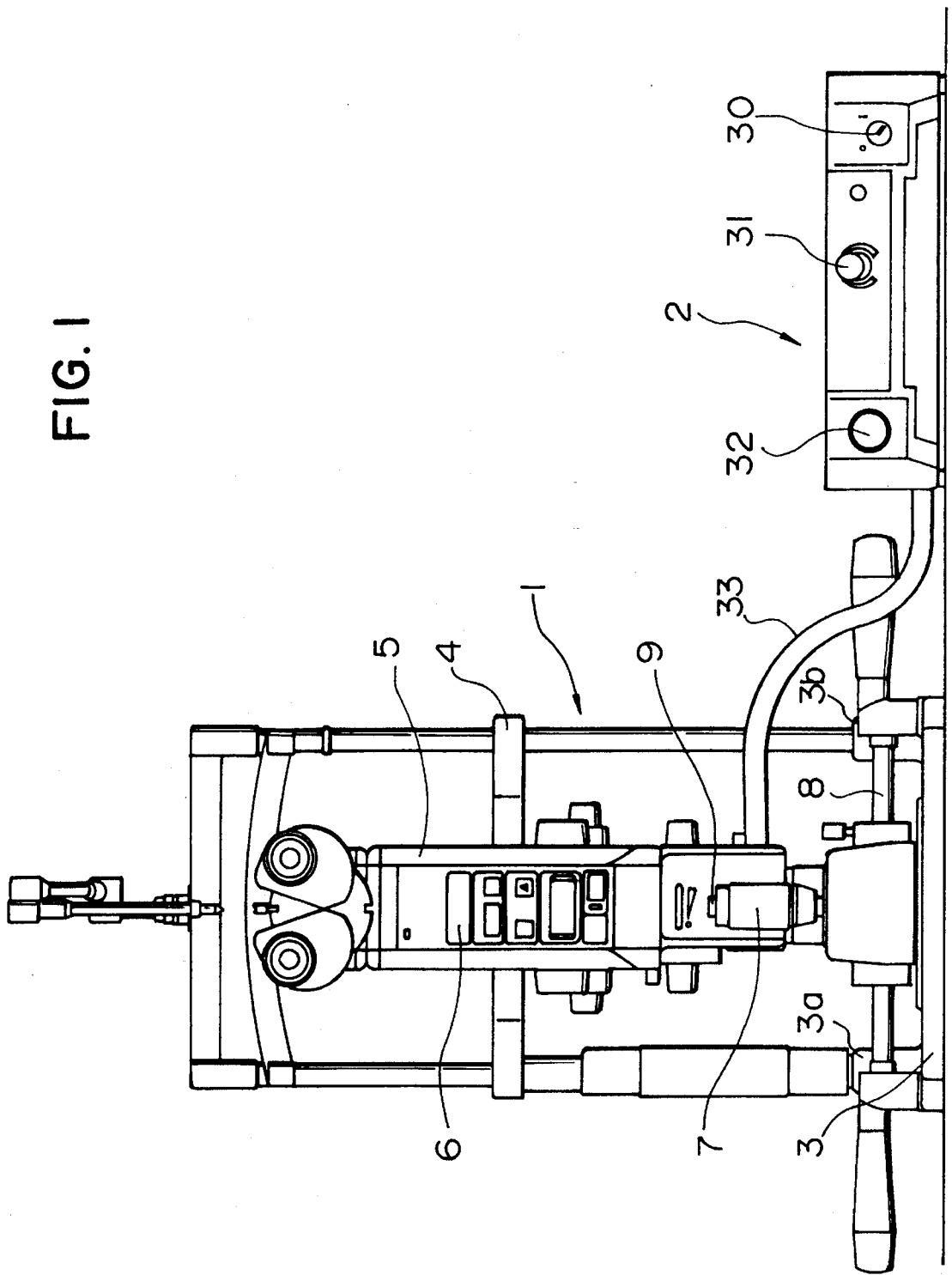
FIG. 1 is a front view showing a slit lamp microscope unit and a power source unit of a laser apparatus for ophthalmological operation according to the present invention.
Figure 2:
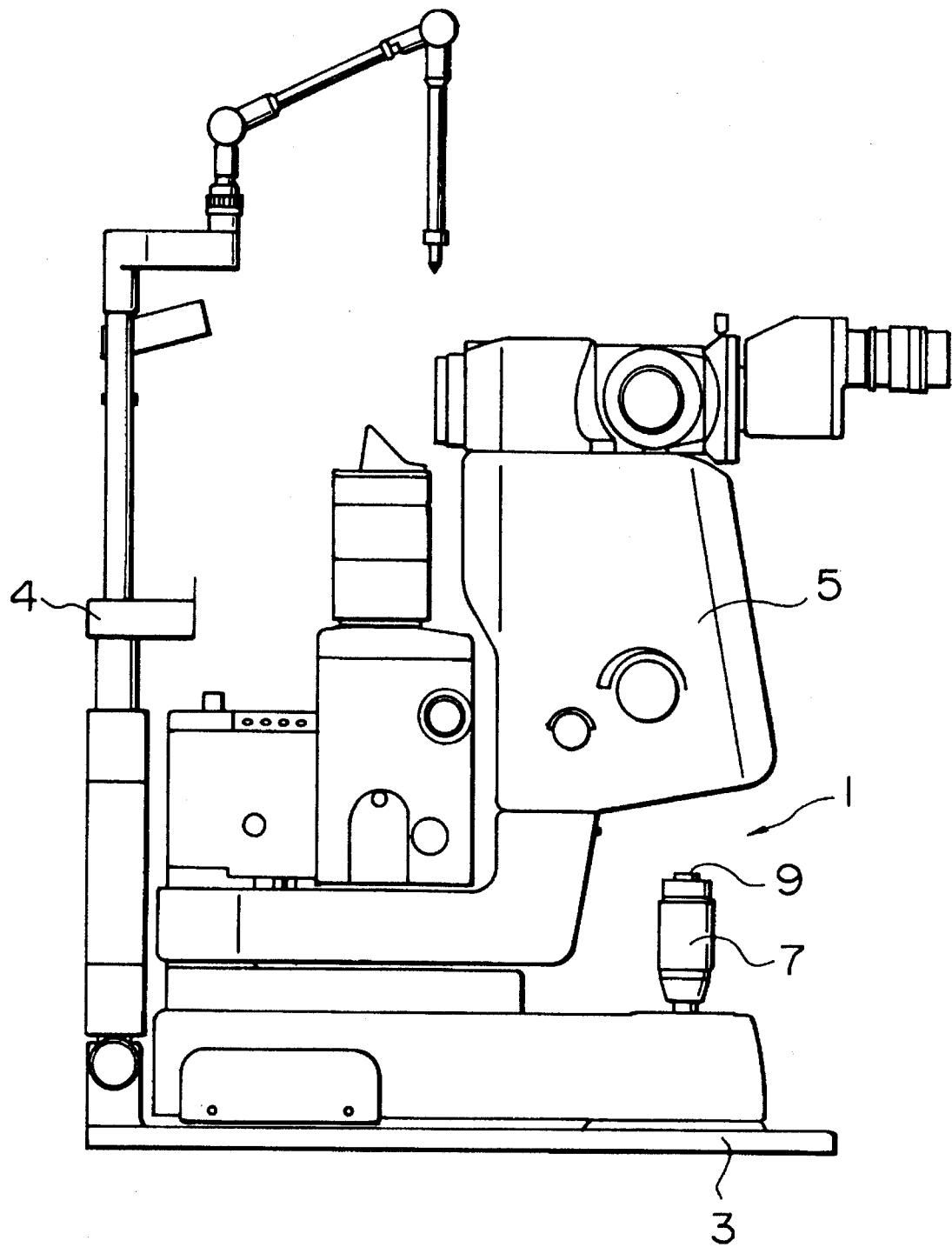
FIG. 2 is a side view of the slit lamp microscope unit in FIG. 1.
Figure 3:
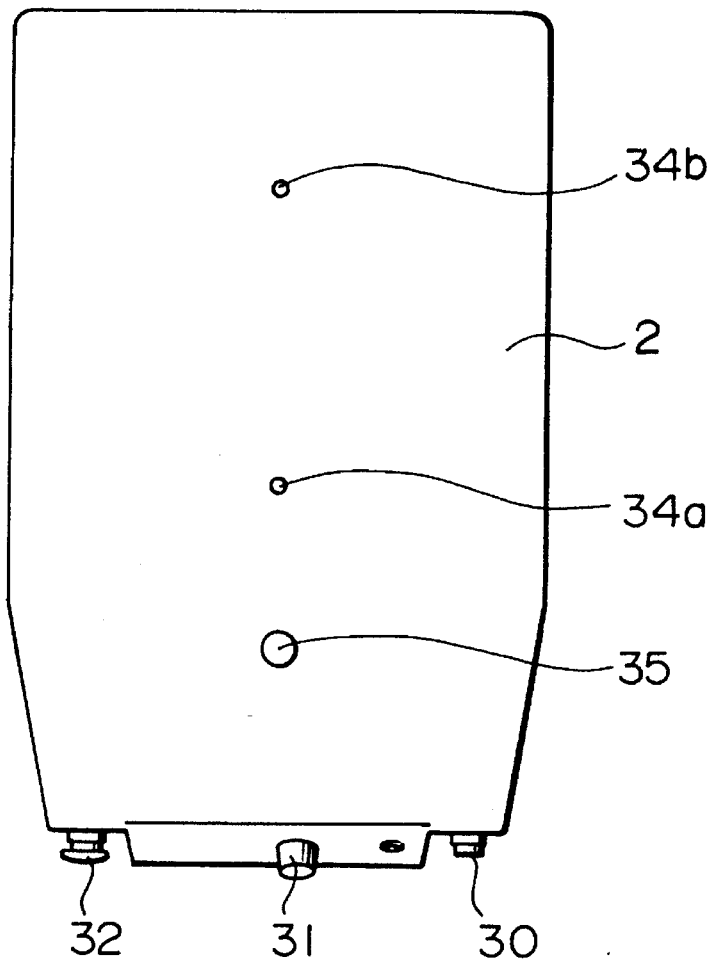
FIG. 3 is a plan view of the power source unit in FIG. 1.
Figure 4:
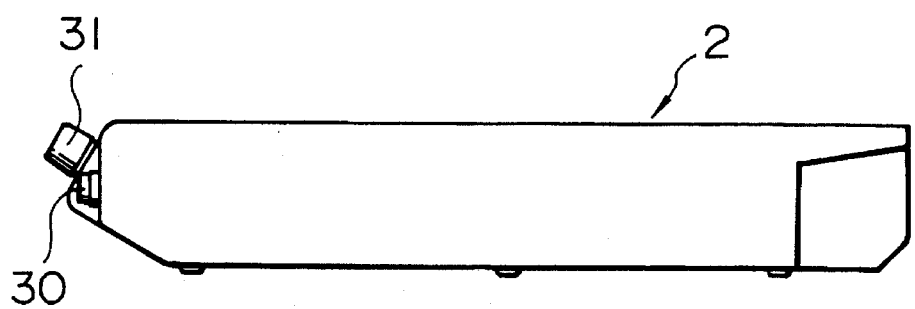
FIG. 4 is a side view of the power source unit in FIG. 1.

FIG. 1 is a front view showing a slit lamp microscope unit 1 and a power source unit 2 of a laser apparatus for ophthalmological operation according to the invention; FIG. 2 is a side view of the slit lamp microscope unit 1 in FIG. 1; FIG. 3 is a plan view of the power source unit 2 in FIG. 1; and FIG. 4 is a side view of the power source unit 2 in FIG. 1.

The slit lamp microscope unit 1 includes a base 3 and a jaw holder 4 on which the head of a patient is fixed, which jaw holder is securely fitted in solid sockets 3a, 3b extending upright from the base 3. A housing 5 for containing an optical system and so forth which will be described later, includes a panel portion 6 consisting of a switch, an indicator, a display and the like. The housing 5 is moved back and forth and to the left and right on the base 3 by a sliding mechanism which is provided below the housing 5. The sliding mechanism comprises a joy stick 7, wheels connected to bearings and a rod 8, and so forth. A trigger switch 9 is provided on the top of the joy stick 7.

Figure 5:
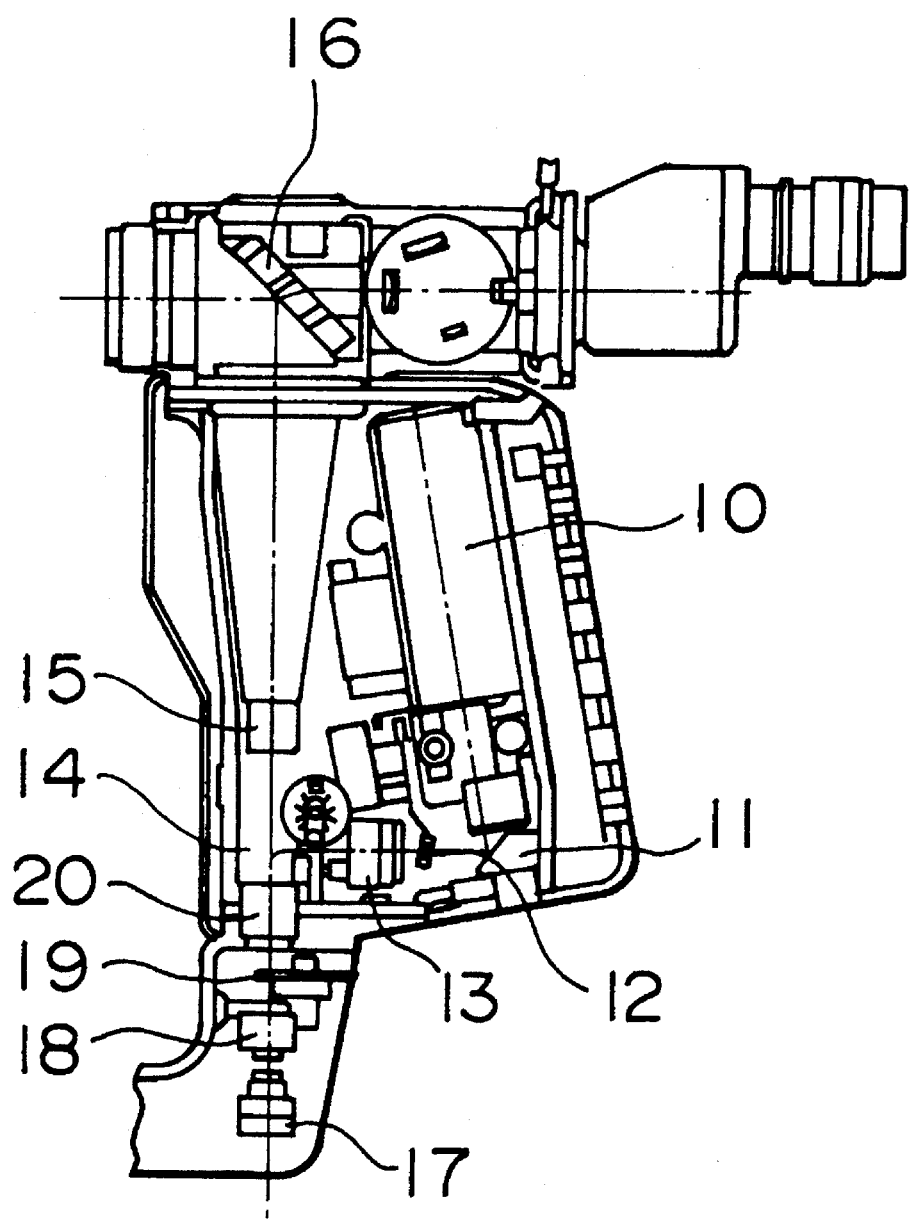
FIG. 5 is a partially broken-away diagram of a housing in FIG. 1.

FIG. 5 is a partially broken-away diagram of the housing 5 which contains the optical system including a YAG laser head 10, a reflection mirror 11 for deflecting a beam emitted from the YAG laser head 10, a shutter 12, a beam expander 13, a dichroic mirror 14 for reflecting a YAG laser beam and transmitting a semiconductor laser beam, a beam expander 15, and a dichroic mirror 16 for reflecting laser light and transmitting visible light.

The optical system further includes a semiconductor laser head 17 for emitting aiming light, a beam expander 18, an attenuator 19 and a beam expander 20.

Beams emitted from the laser heads become coaxial by the dichroic mirror 14 and are reflected by the dichroic mirror 16 to pass between left and right optical axes of observation light and proceed toward an eye to be operated.

As shown in FIGS. 3 and 4, the power source unit 2 contains a source for supplying electrical power to a slit lamp microscope, the laser heads and so forth. Switches such as a key control switch 30, an illumination controller 31 and an emergency switch 32 are provided on the front surface of the power source unit 2. Although not shown, connectors such as a laser head connector, a power connector and a trigger switch connector are also provided on the rear surface of the power source unit 2. Cables for connecting the laser head connector, the trigger switch connector and the like with connectors (not shown) of the slit lamp microscope unit 1 are bundled into one cable 33 at intermediate portions of the cables.

Two holes having internal threads 34a, 34b are formed in the top surface of the power source unit 2. By screw-fasteners which are inserted through attachment holes (not shown) formed in the base 3, into the holes with internal threads 34a, 34b, the base 3 can be secured on the power source unit 2. The top surface of the power source unit 2 is of substantially the same size as the bottom of the base 3. However, the size of the top surface of the power source unit 2 does not matter as long as the base 3 can be steadily mounted on it and the movement of the apparatus is not hindered.

Further, a pin 35 for fixing the power source unit 2 on the bottom surface of a mount table to be described later is provided on the top surface of the power source unit 2. Usually, the pin 35 is screwed inside. When the power source unit 2 is fixed on the bottom surface of the table, the pin 35 is unscrewed to a certain extent to project like a stud so that the top of the pin 35 is inserted in a circular hole formed in the bottom surface of the table, and the top end portion of the inserted pin is supported by a grooved hole integral with the circular hole.

Conditions of use of the above-described apparatus and a carrying method thereof will now be explained.

On such a place as a table where a steady plane can be obtained, the slit lamp microscope unit 1 and the power source unit 2 are mounted in the manner shown in FIG. 1, and can be operated as they are.

Figure 6:
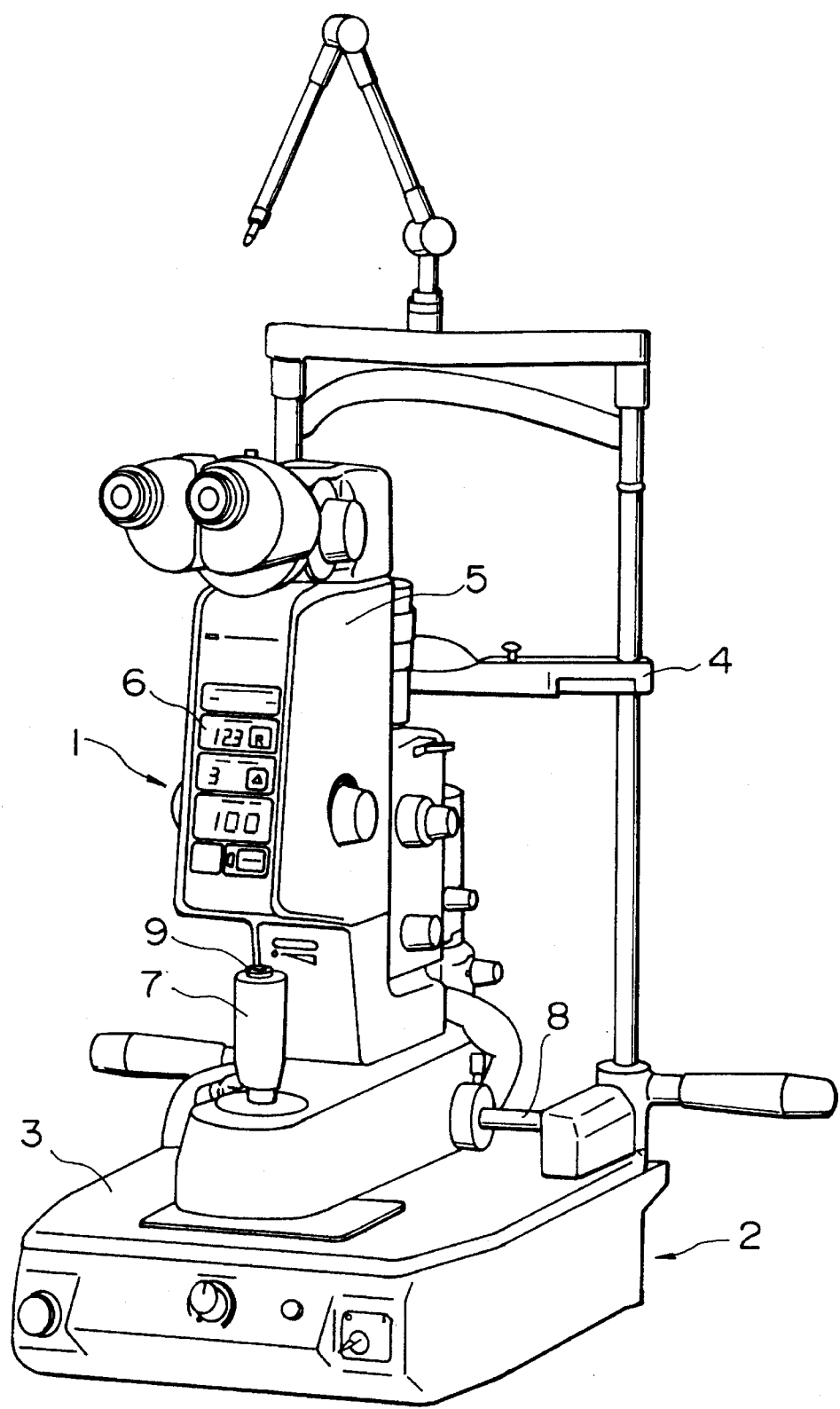
FIG. 6 is a perspective view showing the slit lamp microscope unit and the power source unit in the laser apparatus for ophthalmological operation according to the invention when they are integrally fastened to each other.

Alternatively, the base 3 may be mounted on the top surface of the power source unit 2, and the base 3 and the power source unit 2 may be fixed by screw-fasteners so as to operate the apparatus (see FIG. 6). In this case, a table smaller than that of FIG. 1 can be employed for mounting the power source unit 2 thereon. Thus, the space can be effectively utilized.

Figure 7:
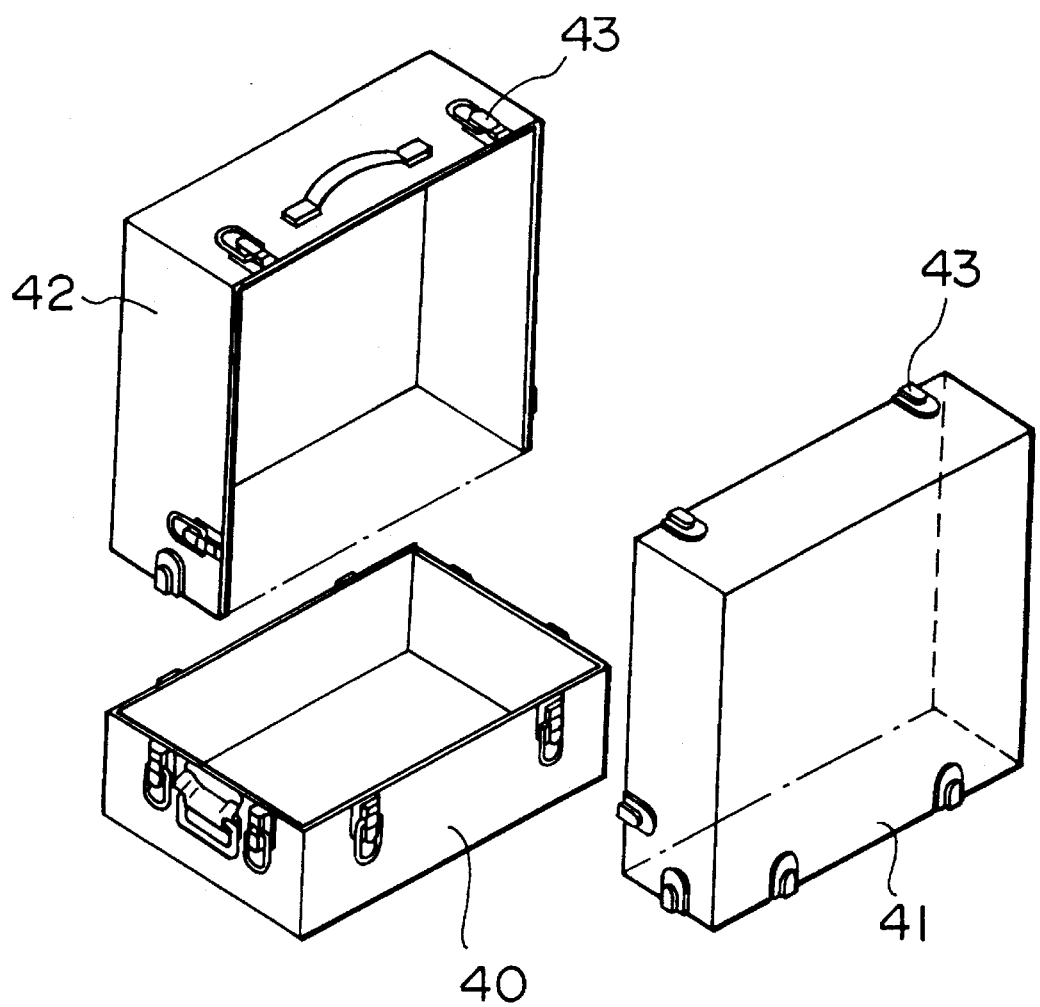
FIG. 7 is a diagram for explaining a structure of a carrying container for the laser apparatus in FIG. 6.

Moreover, the apparatus in the state shown in FIG. 6 can be received, as it is, in a carrying container and carried around. As shown in FIG. 7, the carrying container comprises a lower half 40 and two side halves 41, 42 which are assembled integrally by fastening members 43. The apparatus in this state may be padded and received in the carrying container. However, an ocular portion of the microscope, grips to be held by a patient, and so forth may be detached from the apparatus.

Figure 8:
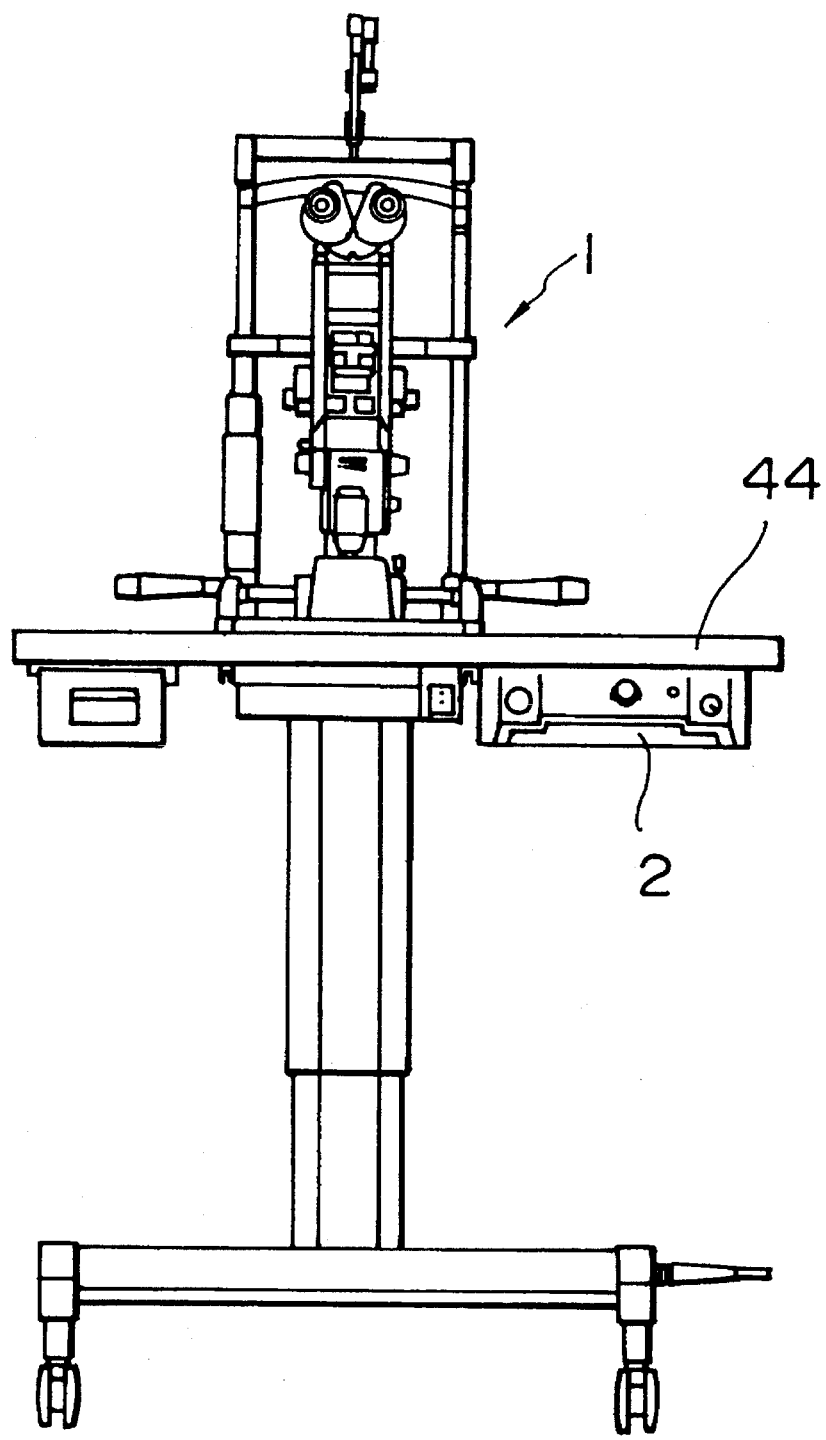
FIG. 8 is a front view showing the laser apparatus according to the invention when it is set on a mount table.
Figure 9:
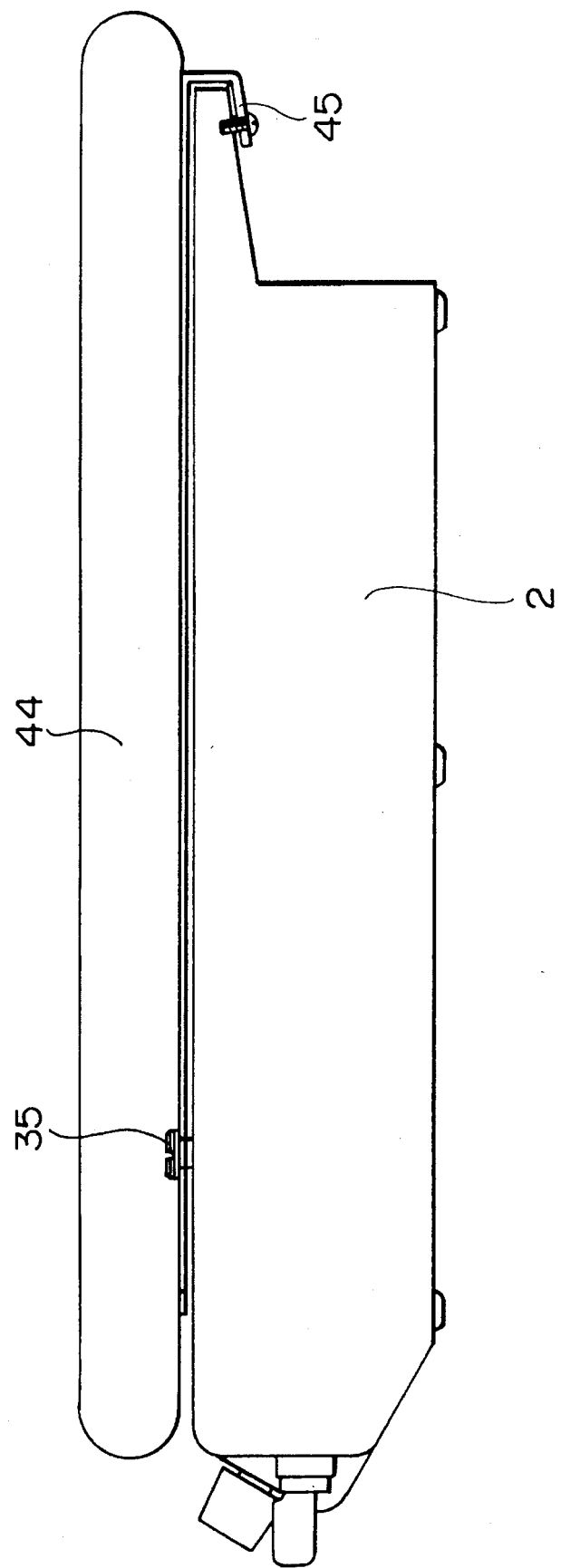
FIG. 9 is a partial side view showing a condition of the power source unit mounted on the mount table.

Furthermore, by preparing a mount table on which the base 3 is placed, the invention apparatus can be used in substantially the same manner as the conventional one, as shown in FIGS. 8 and 9. Holes with internal threads (not shown) equivalent to the two holes with internal threads 34a, 34b of the power source unit 2 are formed in the upper surface of the mount table 44, and the base 3 is fixed on the mount table 44 through the holes with internal threads by screw-fasteners. Also, the power source unit 2 can be secured on the lower side of the mount table 44 by means of the top portion of the pin 35 unscrewed to project like a stud, a grooved hole, and a support member 45 (for fixing the power source unit 2 by screw-fasteners) which is provided on the rear side of the lower surface of the mount table 44.

Figure 10:
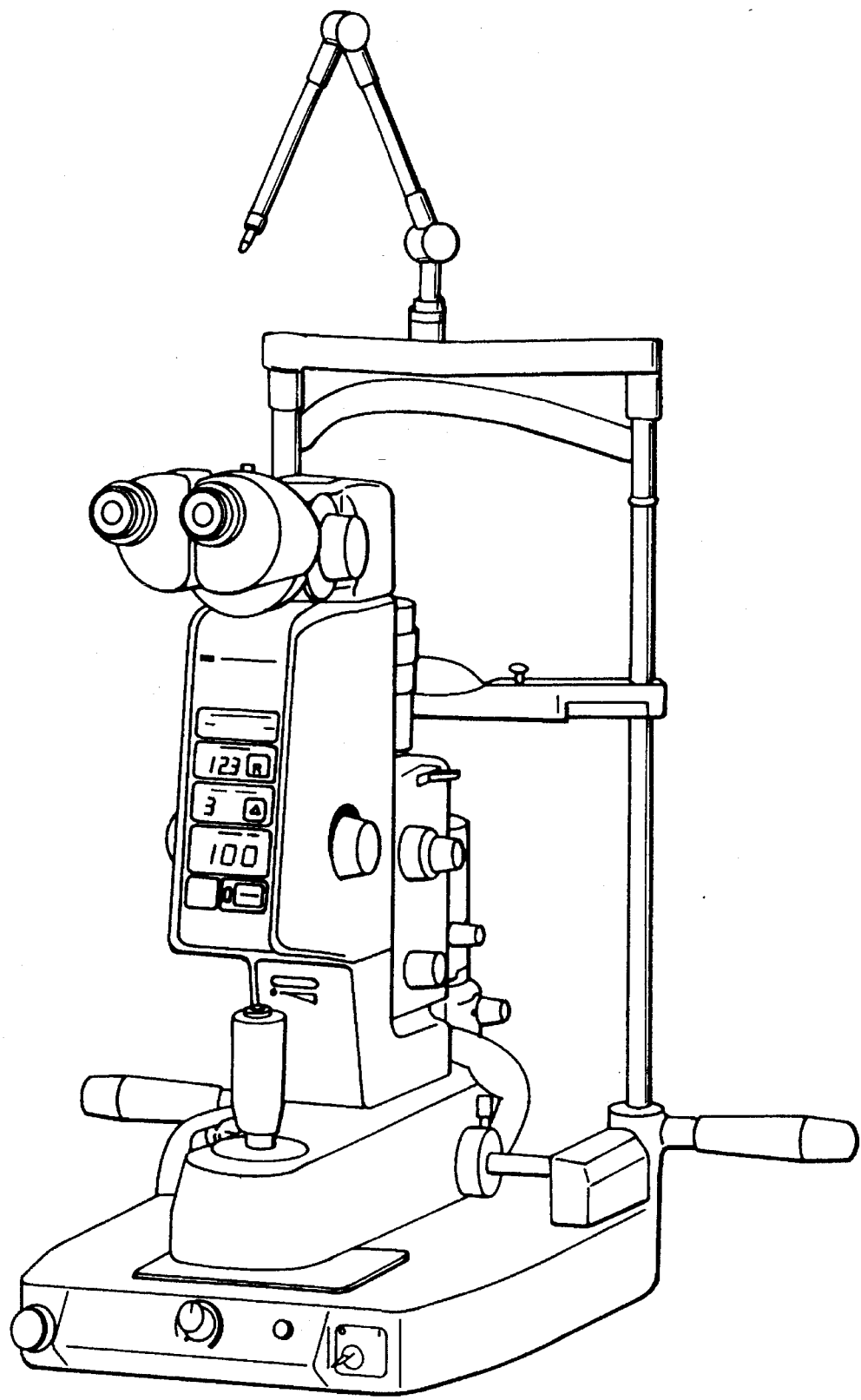
FIG. 10 is a perspective view showing the laser apparatus when the slit lamp microscope unit and the power source unit are constructed integrally.

The above-described embodiment can be modified in various manners. As shown in FIG. 10, the slit lamp microscope and the power source unit may be integrally formed by using the base 3 as a top plate of the power source unit 2. Further, the laser light source and the power source unit may be constructed integrally so that treatment light is guided to the slit lamp microscope unit through an optical cable.

Incidentally, instead of the YAG laser, an argon laser or a semiconductor laser may be used as a laser light source.

According to the present invention, there can be provided a laser apparatus for ophthalmological operation which can be handled readily and carried extremely easily.

What is claimed is:

1. A portable laser apparatus for ophthalmological operation, comprising:

an optical unit, said optical unit including
 i) a slit-lamp microscope unit with an observation optical system for observing an eye to be operated,
 ii) a laser light source secured to said slit-lamp microscope unit,
 iii) a laser light guiding optical system for guiding treatment light emitted from said laser light source toward an affected part of the eye to be operated within an observation visual field of said slit-lamp microscope unit; said portable laser apparatus further comprising a power source housing for containing a power source for supplying electrical power to said optical unit, said power source housing being disposed on a table;

a base with a friction plate which is attached to a top surface of said power source housing;

a slide device which includes a joy stick and slides said slit-lamp microscope unit with respect to said base by operating said joy stick; and conductor cables for connecting said slit-lamp microscope unit and said laser light source to said power source;

said laser apparatus being made easy to carry.

2. A laser apparatus for ophthalmological operation according to claim 1, further including a container exclusively used for carrying the laser apparatus.

3. A laser apparatus for ophthalmological operation according to claim 1, wherein said base and a top plate of said power source housing include means for detachably attaching said base on the top plate.

4. A laser apparatus for ophthalmological operation according to claim 1, wherein said top plate of said power source housing is also used as said base.

5. A laser apparatus for ophthalmological operation according to claim 1, further including a semiconductor light source for emitting an aiming beam which is provided in said slit lamp microscope unit, so that the treatment light and the aiming beam will be made coaxial with each other by a dichroic mirror.

* * * * *